United States Patent [19]

Nishikawa et al.

[11] Patent Number: 5,599,683
[45] Date of Patent: Feb. 4, 1997

[54] METHOD FOR MEASURING PRODUCTION ACTIVITY OF TEST SUBSTANCE TOWARDS FXIIA

[75] Inventors: Katsumi Nishikawa, Katoh-gun; Nobuyuki Ishibashi, Ono, both of Japan

[73] Assignee: Nippon Zoki Pharmaceutical Co., Ltd., Osaka, Japan

[21] Appl. No.: 283,200

[22] Filed: Aug. 4, 1994

[30] Foreign Application Priority Data

Aug. 6, 1993 [JP] Japan ..................... 5-215177

[51] Int. Cl.$^6$ ............................. C12Q 1/56; G01N 33/86
[52] U.S. Cl. ................. 435/13; 435/23; 435/69.2; 436/69
[58] Field of Search ................... 435/13, 23, 24, 435/69.2, 184, 212; 436/69; 530/381

[56] References Cited

U.S. PATENT DOCUMENTS

| | | | |
|---|---|---|---|
| 4,598,043 | 7/1986 | Svendsen | 435/13 |
| 4,985,254 | 1/1991 | Konishi et al. | 424/520 |
| 4,985,354 | 1/1991 | Toyomaki | 435/13 |
| 5,013,558 | 5/1991 | Konishi | 424/520 |
| 5,057,324 | 10/1991 | Shibayama et al. | 424/520 |

FOREIGN PATENT DOCUMENTS

| | | |
|---|---|---|
| 0341209A2 | 11/1989 | European Pat. Off. . |
| 53-101515 | 9/1978 | Japan . |
| 57-77697 | 5/1982 | Japan . |
| 58-35117 | 3/1983 | Japan . |
| 697351 | 9/1953 | United Kingdom . |

OTHER PUBLICATIONS

Kaplan A., Assessment of Hageman Factor . . . Blood 66 (3) 1985 pp. 636–641.
Gallimore M. J., A Direct Chromogenic Peptide . . . J of Fibrinolysis 1(2) 1987 pp. 123–127.
Dumenco L., Inhibition of the Activation of Hageman . . . J Lab Clin Med 112(3) 1988 pp. 394–400.

*Primary Examiner*—Ralph Gitomer
*Attorney, Agent, or Firm*—Fisher, Christen & Sabol

[57] ABSTRACT

The present invention provides a method of measuring the activity of a substance to test how it inhibits or promotes the production of the blood coagulation factor XII in an active form (FXIIa). An activation reaction of the blood coagulation factor XII is initiated by adding a blood coagulation factor XII activator to an animal plasma in the presence of the tested substance. Then the reaction is stopped and the blood coagulation factor XII in an active form (FXIIa) produced in the above reaction is quantitatively determined. FXIIa plays a very important role in the initiation stage in the intrinsic blood clotting system, fibrinolysis system and plasma kallikrein-kinin system. Accordingly, the method of the present invention in which the activity of the tested substance having an inhibiting or promoting action on the production of FXIIa is measured is very highly useful in screening compounds or drugs related to blood clotting and fibrinolysis systems. It may also be used to screen compounds or drugs related to the plasma kallikrein-kinin system such as, for example, blood pressure controlling agents, antiinflammatory agents, analgesics, antiallergic agents, etc.

20 Claims, 3 Drawing Sheets

METHOD FOR MEASURING PRODUCTION ACTIVITY OF TEST SUBSTANCE TOWARDS FXIIA

FIELD OF THE INVENTION

The present invention relates to a method for measuring the activity of a tested substance towards the production of the blood coagulation factor XII in an active form. More particularly, it relates to a method of measuring the activity of a substance which inhibits or promotes the production of the blood coagulation factor XII.

BACKGROUND OF THE INVENTION

The blood coagulation factor XII (hereinafter abbreviated as FXII), which is called a Hageman factor, is a factor which is activated for the first time in the chain reaction of an intrinsic blood clotting. An activated blood coagulation factor XII (the blood coagulation factor XII in an active form, hereinafter abbreviated as FXIIa) activates the blood coagulation factor (FXI). Then, a series of reactions in the reaction system of intrinsic blood clotting as shown in FIG. 1 proceeds. Finally, an insoluble fibrin is produced whereupon the intrinsic blood clotting reaction is accomplished.

A series of the mechanisms or reactions for dissolving the fibrin clot is a fibrinolysis system. FXIIa participates in the initial phase of the fibrinolysis system. Thus, as shown in FIG. 2, plasmin plays a main role in the fibrinolysis. Plasmin is present in plasma as an insoluble plasminogen. However, FXIIa is one of the activators which activate plasminogen to obtain plasmin. The reaction by which the fibrin clot produced as such by coagulation of plasmin is degraded is the final stage of the fibrinolysis system.

In addition, activation of FXII is an initial stage of the plasma kallikrein-kinin system. In the plasma kallikrein-kinin system, it is believed that a series of enzymatic reaction systems takes place as a result of the activation of FXII by injury, invaded stimulation, etc. to the tissues in vivo. Thus, as shown in FIG. 3, the activated FXIIa acts on the plasma prekallikrein which is also present in the plasma, and converts it to a plasma kallikrein which is an enzyme in an active form. Then, the plasma kallikrein acts on the high-molecular-weight kininogen (hereinafter abbreviated as an HK) to liberate bradykinin.

Kinins, such as bradykinin, which are the products in the kallikrein-kinin system exhibit various physiological actions. Examples of the physiological actions are a decrease in blood pressure due to dilation of peripheral blood vessels, promotion of permeability of blood vessels, contraction or relaxation of smooth muscle, induction of pain, induction of inflammation, migration of leucocytes, liberation of catecholamine from the adrenal cortex, etc. Kinins are also known as mediators in acute inflammation including allergic reactions whereby their existence in vivo has a profound significance.

As such, FXIIa is a very important factor in the initial stage of the intrinsic blood clotting system, fibrinolysis system, and plasma kallikrein-kinin system. Accordingly, substances which affect the production of FXIIa may be useful pharmaceuticals or drugs in the areas of blood clotting and fibrinolysis. In addition, substances which affect the production of FXIIa may be useful as antiinflammatory, analgesic, and antiallergic drugs because bradykinin liberated in the plasma kallikrein-kinin system has various physiological activities as mentioned above.

The present invention provides a method for determining the action and activity of a substance which inhibits or promotes the production of FXIIa which is an initiation factor of the intrinsic blood clotting system, fibrinolysis system and plasma kallikrein-kinin system in a simple, convenient, prompt and precise manner. The method is a very effective means for ascertaining the action helpful in adjusting the bioregulations as mentioned above and also for developing such drugs.

SUMMARY OF THE INVENTION

The present invention provides an in vitro method of measuring the activity of a test substance with respect to inhibiting or promoting the production of the blood coagulation factor XII in active form (FXIIa). The tested substance's ability to inhibit or promote the production of FXIIa which participates in various physiological reaction systems in vivo is measured in a simple, convenient, prompt and precise manner. The measuring method may be used to screen tested substances for usefulness as pharmaceuticals or drugs for controlling blood clotting, blood pressure, and fibrinolysis. Screening of tested substances for use as anti-inflammatory drugs, analgesics, and antiallergic drugs may also be performed.

To measure the activity of a test substance in accordance with the method of the present invention, an activation reaction of a blood coagulation factor XII is initiated. Initiation may be achieved by adding a blood coagulation factor XII activator to animal plasma in the presence of the test substance. Then, the reaction is stopped and the blood coagulation factor XII in an active form produced in the above reaction is quantitatively determined. The amount of FXIIa produced relative to the amount produced in a control sample which does not contain the tested substance or which contains a different test substance may be used to indicate the relative activity of the tested substance.

DETAILED DESCRIPTION OF THE INVENTION

Figure 1:
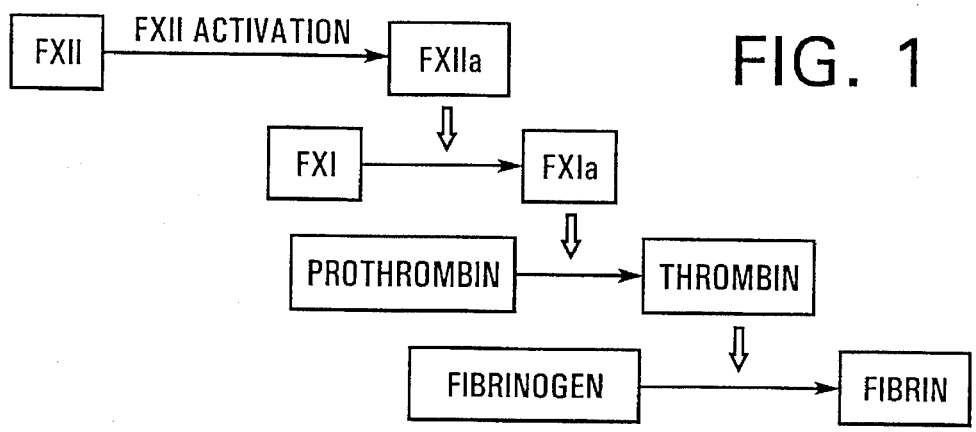
FIG. 1 is a schematic diagram illustrating the regulation mechanism in vivo wherein FXIIa participates in the intrinsic blood clotting system.
Figure 2:
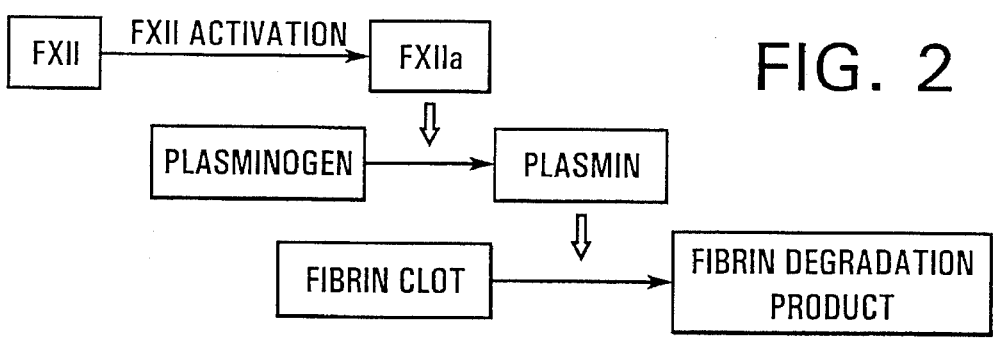
FIG. 2 is a schematic diagram illustrating the regulation mechanism in vivo wherein FXIIa participates in the fibrinolysis system.

In the present invention, a substance is tested for its ability to inhibit or promote the production of the blood coagulation factor XII in active form (FXIIa). The test may be conducted in vitro by admixing a blood coagulation factor XII activator with a blood coagulation factor II (FXII) to initiate activation of the FXII in the presence of the substance. The blood coagulation factor XII (FXII) may be present in the plasma of an animal. The reaction is stopped and the amount of FXIIa is quantitatively determined as an indication of the effectiveness or activity of the tested substance in promoting or inhibiting the production of FXIIa in a physiological reaction system involving FXII. The effect of the tested substances on production of FXIIa may be used to screen them for usefulness as antiinflammatory, analgesic, and antiallergic drugs and as pharmaceuticals for controlling blood pressure, blood clotting, and fibrinolysis.

With respect to the plasma of animals which can be used in the measuring method of the present invention, the plasma of any animal will do provided it has a blood clotting system and a plasma kallikrein-kinin system. For example, human plasma and plasma of cattle and experimental animals such as cows, sheep, pigs, horses, goats, monkeys, dogs, cats, rabbits, guinea pigs, hamsters, rats or mice may be utilized. Preferably, human plasma is used in the methods of the present invention.

The plasma may be used in the form of a preparation manufactured by common methods. For example, a citric acid-added plasma prepared by collecting blood in the presence of citric acid followed by centrifuging may be used. Alternatively, freeze-dried plasma which is manufactured by conventional methods may be used as well. The animal plasma prepared as such may be used as it is or may be diluted, if desired, to control the reaction rate.

With reference to the FXII activator, any substance may be used provided it exhibits an activating action for FXII. Examples of substances which may be used as an FXII activator are glass, kaolin, celite, collagen, homocystine, sodium urate, cell components such as membranes of platelets and other cells, fibronectin, elaidic acid, quercetin, rutin, sulfated glycolipids, proteoglycan, mucopolysaccharides, sodium stearate, dextran sulfate, amylose sulfate, carrageenin and proteases which activate FXII by a restricted decomposition. They may be used either solely or jointly and the concentration of such FXII activators may be selected in effective concentrations for activating FXII.

The mixing reaction of the animal plasma, FXII activator and tested substance is preferably carried out at 0° C. to 4° C. so that the intrinsic inhibitor hardly acts and, in addition, the progress of the reaction can be easily controlled. The pH during the reaction may be suitably selected to promote the activation reaction. When human plasma is used, it is preferred to carry out the reaction at pH 7.0 to 9.0. Further, in order to obtain an optimum reaction condition, salts such as sodium chloride, metal ions such as zinc ion and other additives and auxiliary agents which are commonly used in this art may be added to the reaction system.

The reaction time may be selected depending upon the amount of the animal plasma, concentrations of the FXII activators and the tested substance, pH of the reaction solution, etc. When, however, production of the FXIIa is saturated, it is no longer possible to precisely evaluate the action of the tested substance. Accordingly, it is preferred to set the reaction time so that it is before the production of FXIIa is saturated, i.e, within a time where there is a clear positive relationship between the reaction time and the produced FXIIa. Preferably in terms of the evaluation, the reaction time is within a time where a substantially linearly proportional relationship exists between the reaction time and the amount of FXIIa produced.

With respect to a method for stopping the above-mentioned FXII activation reaction, it is preferred to use a substance which stops the production of FXIIa in the reaction, for example an inhibitor for activation of FXII such as polybren and an inhibitor which specifically inhibits the plasma kallikrein, most preferably a plasma kallikrein inhibitor which does not substantially affect FXIIa such as SBTI. SBTI (soy bean trypsin inhibitor) is a trypsin inhibitor prepared from soy bean. When the FXII activation reaction is stopped, the produced FXIIa can be quantitatively determined utilizing an enzymatic activity of FXIIa as a target by using a substrate to FXIIa. The concentrations of the inhibitors, such as polybren and SBTI, may be suitably selected within such an extent that they do not substantially affect the FXIIa activity.

Figure 3:
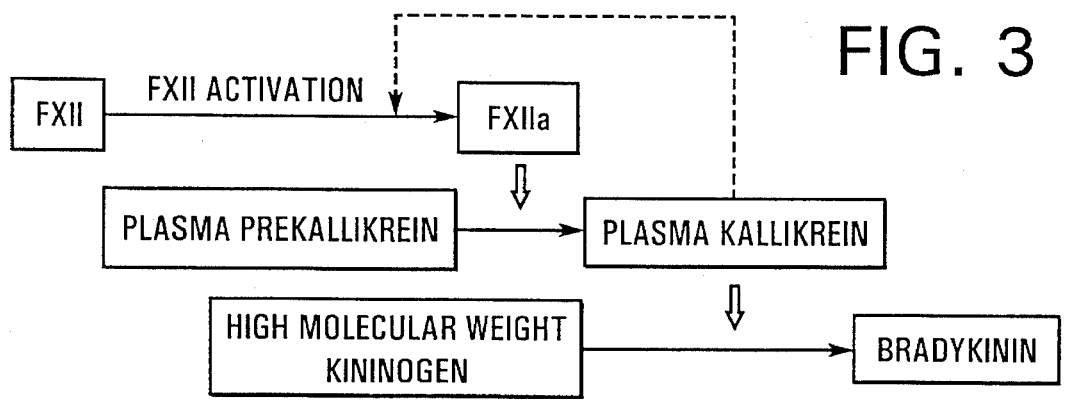
FIG. 3 is a schematic diagram illustrating the regulation mechanism in vivo wherein FXIIa participates in the plasma kallikrein-kinin system.

In the plasma kallikrein-kinin system, as shown in FIG. 3 there is a feedback mechanism wherein the production of FXIIa is promoted by the produced plasma kallikrein. However, the activity of the tested substance towards the production of FXIIa by a pure FXIIa activation reaction which does not proceed through said feedback mechanism may be determined by the present invention as well. In the latter case the animal plasma which is used in the method of the present invention is: (a) plasma in which plasma prekallikrein is in a substantially deficient state prepared by adding an inhibitor which is specific to the plasma kallikrein, such as the above-mentioned SBTI, to the reaction system prior to the activation of FXII, or (b) prekallikrein-deficient plasma per se or that which is made into a substantially prekallikrein-deficient state by removing or inactivating the plasma prekallikrein in normal plasma.

The quantitative determination of the produced FXIIa can be carried out by conventional methods. For example, a method in which the measurement is conducted using a substrate to FXIIa and utilizing an enzymatic activity of FXIIa may be used. Known methods using natural substrates such as plasma prekallikrein, blood coagulation factor XI or plasmin, coloring synthetic substrates such as D-Pro-Phe-Arg-pNA and D-Leu-Gly-Arg-pNA, or fluorescent synthetic substrates such as Boc-Glu(OBz)-Gly-Arg-MCA or Boc-Gln- Gly-Arg-MCA provide easy and simple ways for the quantitative determination of FXIIa produced. Besides the above-mentioned measuring methods using substrates, immunological measuring methods such as radioimmunoassay (RIA), enzyme immunoassay (EIA), etc., a quantitative analytical method utilizing chromatography, and the like may be used as well in the present invention.

The present invention is further illustrated by the following example:

EXAMPLE

To a solution comprising diluted human plasma, a certain amount of a substance to be tested (an analyte), and 25 mM Tris hydrochloride buffer (pH: 8) containing 90 mM NaCl was added dextran sulfate to make its final concentration 2 micrograms/liter. The mixture was incubated in ice water for 15 minutes and then polyburene and SBTI were added thereto to make their final concentrations 200 micrograms/ ml and 40 micrograms/ml, respectively. The reaction solution was incubated in a Tris hydrochloride buffer (pH: 8) together with 1 mM of D-Pro-Phe-Arg-pNA at 30° C. for 30 minutes. The reaction was stopped by adding citric acid to the reaction solution. The mixture was centrifuged at 3,000 rpm for ten minutes and the absorbance (which corresponds to the produced amount of FXIIa) of the resulting supernatant liquid at 405 nm was measured.

Figure 4:
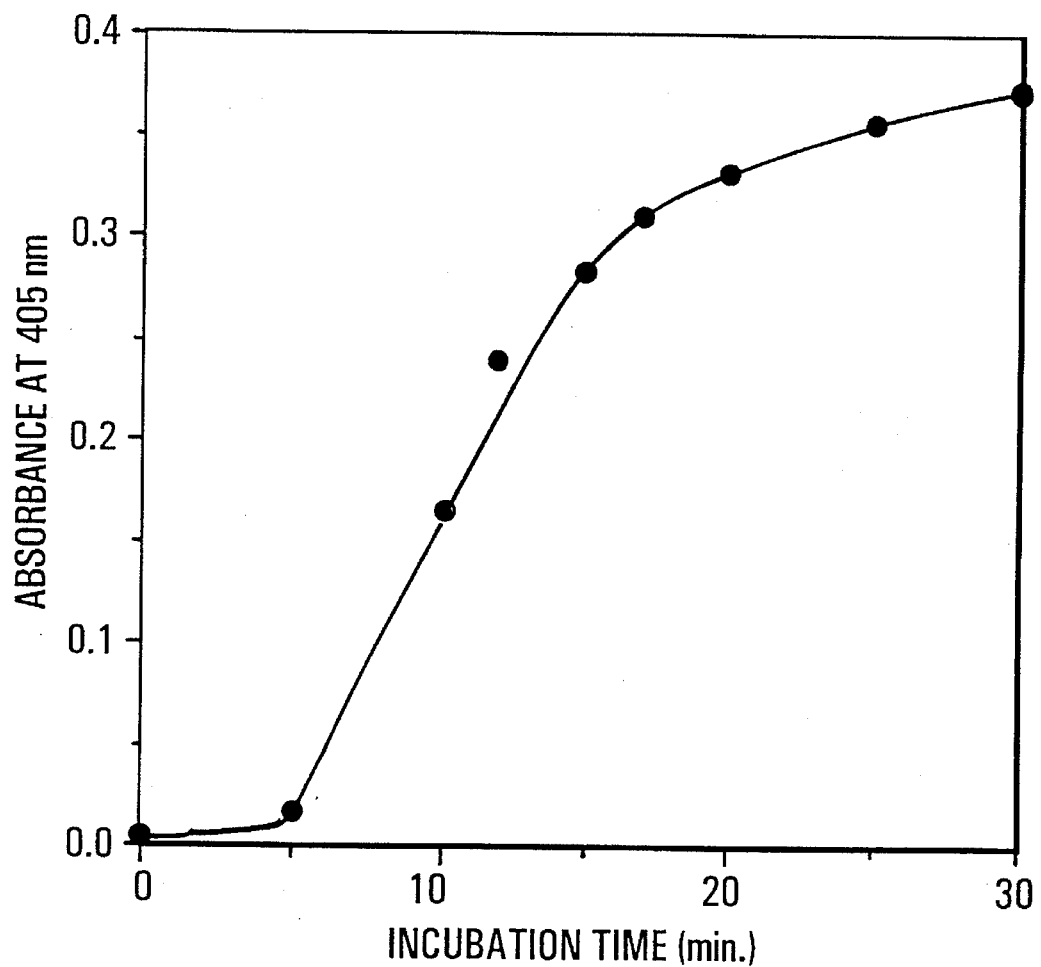
FIG. 4 is a graph showing the changes in the absorbance as a function of incubation time in the measuring method of the present invention wherein the absorbance corresponds to the amount of FXIIa produced in the Example.

FIG. 4 shows the changes in the absorbances when the incubating time at 0° C. in the above reaction for producing FXIIa is changed. In FIG. 4, the abscissa shows the incubating time (minutes) at 0° C. while the ordinate shows the absorbance at 405 nm. In FIG. 4, FXIIa is produced in almost linearly increasing amount with lapse of time until the incubating time reaches about 17 minutes. Therefore, it is preferred that the incubating time is set to be between 0 to 17 minutes.

Figure 5:
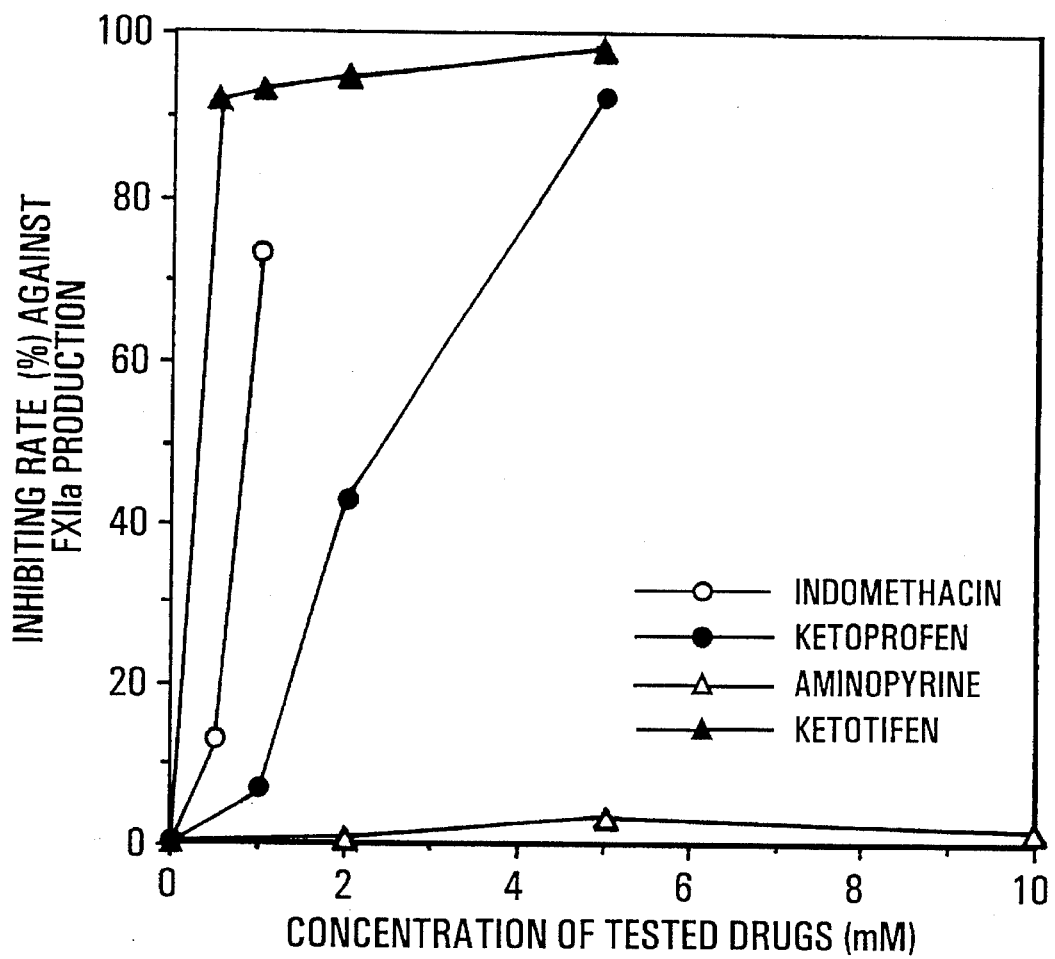
FIG. 5 is a graph showing the results in the measurement of the inhibiting activity of the tested substances of the Example towards the production of FXIIa using the activity measuring method of the present invention.

FIG. 5 shows the results of the measurement of the inhibiting activity of four test drugs which are used as analgesic or antiallergic agents (indomethacin, ketoprofen, aminopyrine and ketotifen) to the production of FXIIa in accordance with the measuring method of the present invention. In FIG. 5, the abscissa shows the concentration (mM) of the drugs tested while the ordinate shows the inhibiting rate (%) to the production of FXIIa.

FXIIa plays a very important role in the initiation stage of the intrinsic blood clotting system, fibrinolysis system and plasma kallikrein-kinin system. Accordingly, the method of the present invention in which the activity of a tested substance having an action of inhibiting or promoting the FXIIa production can be measured is very highly useful in screening drugs related to the blood clotting system and the plasma kallikrein-kinin system such as blood pressure controlling agents, antiinflammatory agents, analgesics, antiallergic agents, etc.

Further in accordance with the measuring method of the present invention, the feedback mechanism of plasma kallikrein for FXIIa production is secured whereby it is possible to screen drugs which solely relate to the activating stage of FXII which is the initiation stage of the reaction in the intrinsic blood clotting system, fibrinolysis system, plasma kallikrein-kinin system, etc. Consequently, screening of drugs based upon a clear and specific action mechanism is now possible and the present invention has significant merit for the development of various new drugs.

What is claimed is:

1. A method for measuring activity of a test substance towards production of blood coagulation factor XII in an active form comprising initiating an activation reaction of blood coagulation factor XII by admixing a blood coagulation factor XII activator with an animal plasma in the presence of the test substance to produce an amount of blood coagulation factor XII in an active form, then stopping the reaction by adding both an inhibitor which inhibits activation of the blood coagulation factor XII and an inhibitor which specifically inhibits plasma kallikrein, said adding being within a time wherein the amount of blood coagulation factor XII in an active form which is produced increases with increasing reaction time, and quantitatively determining the amount of blood coagulation factor XII in an active form produced in said activation reaction as a measure of the activity of the test substance.

2. A method according to claim 1 wherein the amount of blood coagulation factor XII in an active form produced in said activation reaction is quantitatively determined by admixing the blood Coagulation factor XII in an active form with a substrate to the blood coagulation factor XII in an active form.

3. A method according to claim 2 wherein said substrate is a synthetic substrate to the blood coagulation factor XII in an active form.

4. A method as claimed in claim 1 wherein said animal plasma is human plasma.

5. A method as claimed in claim 1 wherein said animal plasma is a citric acid-added plasma.

6. A method as claimed in claim 1 wherein said activator is at least one member selected from the group consisting of glass, kaolin, celite, collagen, homocystine, sodium urate, cell components of platelets, fibronectin, elaidic acid, quercetin, rutin, sulfated glycolipids, proteoglycan, mucopolysaccharides, sodium stearate, dextran sulfate, amylose sulfate, carrageenin and proteases which activate the blood coagulation factor XII by a restricted decomposition.

7. A method as claimed in claim 1 wherein the activation reaction is stopped within a period of time during which the amount of blood coagulation factor in an active form which is produced is substantially linear with respect to reaction time.

8. A method as claimed in claim 1 wherein said activation reaction is stopped by polybren and soybean trypsin inhibitor.

9. A method as claimed in claim 1 wherein the blood coagulation factor XII is prevented from being produced in its active form via a plasma kallikrein-kinin feedback mechanism by either:

(i) adding an inhibitor specific to plasma kallikrein prior to the activation of the blood coagulation factor XII, or (ii) removing or deactivating plasma prekallikrein in the plasma, or (iii) admixing said blood coagulation factor XII activator with a prekallikrein-deficient animal plasma.

10. A method as claimed in claim 9 wherein the blood coagulation factor XII is prevented from being produced in its active form via the plasma kallikrein-kinin feedback mechanism by adding soybean trypsin inhibitor prior to activation of the blood coagulation factor XII.

11. A method for screening a drug for activity of the drug towards production of blood coagulation factor XII in an active form comprising: (a) admixing a blood coagulation factor XII activator with an animal plasma to initiate a first activation of the blood coagulation factor XII in the presence of the drug to produce an amount of blood coagulation factor XII in an active form, then stopping the first activation of the blood coagulation factor XII by adding both an inhibitor which inhibits activation of the blood coagulation factor XII and an inhibitor which specifically inhibits plasma kallikrein, said adding being within a time wherein the amount of blood coagulation factor XII in an active form which is produced increases with increasing reaction time, and quantitatively determining the amount of blood coagulation factor XII in an active form produced in the first activation, (b) admixing said blood coagulation factor XII activator with said animal plasma to initiate a second activation of the blood coagulation factor XII in the absence of said drug to produce an amount of blood coagulation factor XII in an active form, then stopping the second activation of the blood coagulation factor XII by adding both an inhibitor which inhibits activation of the blood coagulation factor XII and an inhibitor which specifically inhibits plasma kallikrein, said adding being within a time wherein the amount of blood coagulation factor XII in an active form which is produced increases with increasing reaction time, and quantitatively determining the amount of blood coagulation factor XII in an active form produced in the second activation, and (c) comparing the amounts of blood coagulation factor XII in an active form produced in said first activation and said second activation to obtain a relative activity of said drug towards the production of said blood coagulation factor in an active form.

12. A method as claimed in claim 11 wherein the drug is related to blood clotting.

13. A method as claimed in claim 11 wherein the drug is related to fibrinolysis.

14. A method as claimed in claim 11 wherein the drug is screened for utility as a blood pressure controlling agent.

15. A method as claimed in claim 11 wherein the drug is screened for utility as an antiinflammatory agent.

16. A method as claimed in claim 11 wherein the drug is screened for utility as an antiallergic agent.

17. A method as claimed in claim 11 wherein the drug is screened for utility as an analgesic.

18. A method for measuring activity of a test substance towards production of blood coagulation factor XII in an active form comprising: (a) initiating a first activation reaction of blood coagulation factor XII by admixing a blood coagulation factor XII activator with an animal plasma in the presence of the test substance to produce an amount of blood coagulation factor XII in an active form, then stopping the reaction by adding both an inhibitor which inhibits activation of the blood coagulation factor XII and an inhibitor which specifically inhibits plasma kallikrein, said adding being within a time wherein the amount of blood coagulation factor XII in an active form which is produced increases with increasing reaction time, and quantitatively determining the amount of blood coagulation factor XII in an active form produced in said first activation reaction, (b) initiating a second activation reaction of said blood coagulation factor XII by admixing said blood coagulation factor XII activator with said animal plasma in the absence of said test substance to produce an amount of blood coagulation factor XII in an active form, then stopping the reaction by adding both an inhibitor which inhibits activation of the blood coagulation factor XII and an inhibitor which specifically inhibits plasma kallikrein, said adding being within a time wherein the amount of blood coagulation factor XII in an active form which is produced increases with increasing reaction time, and quantitatively determining the amount of blood coagulation factor XII in an active form produced in said second activation reaction, and (c) comparing the amounts of blood coagulation factor XII in an active form produced in said first activation reaction and said second activation reaction to obtain the activity of said substance towards the production of said blood coagulation factor XII in an active form.

19. A method according to claim 18 wherein the amounts of blood coagulation factor XII in an active form produced in said first and said second activation reactions are quantitatively determined by admixing the blood coagulation factor XII in an active form with a substrate to the blood coagulation factor XII in an active form.

20. A method according to claim 19 wherein said substrate is a synthetic substrate to the blood coagulation factor XII in an active form.

* * * * *